(12) United States Patent
Clark et al.

(10) Patent No.: US 11,871,930 B2
(45) Date of Patent: Jan. 16, 2024

(54) ANTI-SLIP LIGATION BANDS

(71) Applicants: United States Endoscopy Group, Inc., Mentor, OH (US); Melissa Clark, Clemmons, NC (US); Fritz Haller, Clemmons, NC (US)

(72) Inventors: Melissa Clark, Clemmons, NC (US); Fritz Haller, Clemmons, NC (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 262 days.

(21) Appl. No.: 16/964,840

(22) PCT Filed: Jan. 24, 2019

(86) PCT No.: PCT/US2019/014983
§ 371 (c)(1),
(2) Date: Jul. 24, 2020

(87) PCT Pub. No.: WO2019/147835
PCT Pub. Date: Aug. 1, 2019

(65) Prior Publication Data
US 2021/0059682 A1    Mar. 4, 2021

Related U.S. Application Data

(60) Provisional application No. 62/622,345, filed on Jan. 26, 2018.

(51) Int. Cl.
*A61B 17/12* (2006.01)
*A61B 17/00* (2006.01)

(52) U.S. Cl.
CPC ............ *A61B 17/12009* (2013.01); *A61B 2017/00858* (2013.01); *A61B 2017/12018* (2013.01)

(58) Field of Classification Search
CPC .... A61B 17/12009; A61B 2017/00858; A61B 2017/12018; A61B 17/12013
USPC ................................................ 606/140, 141
See application file for complete search history.

(56) References Cited

U.S. PATENT DOCUMENTS

| 5,009,251 A | 4/1991 | Pike et al. |
| 5,972,009 A * | 10/1999 | Fortier ............. A61B 17/12013 606/151 |
| D753,274 S * | 4/2016 | Young ......................... D23/269 |
| 2003/0097141 A1 | 5/2003 | Adams et al. |

(Continued)

OTHER PUBLICATIONS

International Search Report and Written Opinion of International Application No. PCT/US2019/014983 dated Jul. 1, 2019, 8 pages.

(Continued)

*Primary Examiner* — Kathleen S Holwerda
*Assistant Examiner* — Serenity A Miller
(74) *Attorney, Agent, or Firm* — Calfee, Halter & Griswold LLP

(57) ABSTRACT

Ligation bands are provided having improved compression and anti-slip properties. For example, a ligation band can be provide with a substantially ring-shaped elastic body that has a first tissue-contacting surface, a second tissue-contacting surface opposite the first tissue-contacting surface, and an aperture that extends therethrough. At least one of the tissue-contacting surfaces can have a plurality of protrusions that define an interlinking web-pattern with a plurality of recesses.

15 Claims, 13 Drawing Sheets

(56) References Cited

U.S. PATENT DOCUMENTS

| | | |
|---|---|---|
| 2009/0105728 A1 | 4/2009 | Noda et al. |
| 2010/0063517 A1 | 3/2010 | Cleator |
| 2013/0228984 A1 | 9/2013 | Watanabe |
| 2013/0341874 A1 | 12/2013 | Aykanat et al. |
| 2014/0276407 A1 | 9/2014 | Devries |
| 2015/0018848 A1 | 1/2015 | Kappel et al. |
| 2017/0000637 A1 | 1/2017 | Crews et al. |
| 2017/0290591 A1 | 10/2017 | Liddicoat et al. |

OTHER PUBLICATIONS

Extended Search Report from European Application No. 19743784.1 dated Sep. 23, 2021 (8 pages).

* cited by examiner

ANTI-SLIP LIGATION BANDS

CROSS-REFERENCE TO RELATED APPLICATIONS

The present application is a national stage application of PCT/US19/14983, which claims the benefit of U.S. Provisional Application 62/622,345 filed on Jan. 26, 2018. The entire contents of these applications are incorporated herein by reference in their entirety.

FIELD

Ligation bands are provided having improved compression and anti-slip properties.

BACKGROUND

Ligation is a procedure in which a thread, wire, or band is applied around a tissue structure or area to constrict it, thereby preventing flow of blood or other body fluids. Band ligation involves applying a highly elastic band around a tissue site to ensnare and constrict it, leading to strangulation, sloughing, and ligation of the ensnared tissue. Ligation may be used to treat varices, polyps, hemorrhoids, or other lesions.

As such, for an effective ligation of tissue, the bands should have sufficient elasticity and gripping force to avoid band slippage during and after deployment around tissue. Currently, a large number of complications in ligation operations stem from band slippage, such as the interaction of the bands with the barrel (band deployment issues) and/or the bands with the tissue (band slippage issues).

Accordingly, there remains a need for improved ligation bands.

SUMMARY

Methods, devices, and systems are provided herein for ligation bands that resist slipping once deployed around tissue.

In one aspect, a ligation band is provided that has a substantially ring-shaped elastic body with a first tissue-contacting surface, a second tissue-contacting surface opposite the first tissue-contacting surface, and an aperture that extends therethrough. At least one of the tissue-contacting surfaces has a plurality of protrusions formed thereon that define an interlinking web-pattern with a plurality of recesses therebetween.

The ligation band can have numerous variations. For example, the plurality of protrusions can be configured to resist expansion and deformation of the elastic body. The elastic body can also be latex free. In another example, the plurality of protrusions can be in a repeating delta pattern. The plurality of protrusions can be on both the first and second tissue-contacting surfaces. The aperture can also be substantially cylindrical with smooth inner-facing sidewalls.

In some embodiments, the ligation band can have a compression force of at least about 5.5 N when expanded to 7.5 mm. In another example, the ligation band can have a compression force of at least about 6.5 N when expanded to 9 mm. An average cross linked band grip force of the ligation band can be at least about 0.50 N.

In another aspect, a ligation band is provided that has a substantially ring-shaped elastic body with first and second tissue-contacting surfaces thereon and a central opening extending therethrough. Each of the first and second tissue-contacting surfaces have four delta-shaped protrusions that extend therefrom, and the delta-shaped protrusions are spaced around the central opening. Each delta-shaped protrusion defines a substantially delta-shaped recess therein and is configured to grip tissue.

The band can have several variations. For example, the four delta-shaped protrusions can define an interlinking web-pattern. In another example, the four delta-shaped protrusions can be configured to resist expansion and deformation. The band can also include 3 perimeter recesses formed between each adjacent delta-shaped protrusion on the first and second tissue-contacting surfaces. In another example, each delta-shaped protrusion can have an apex oriented away from the central opening.

In some examples, the ligation band can have a compression force of at least about 5.5 N when expanded to 7.5 mm. In another example, the ligation band can have a compression force of at least about 6.5 N when expanded to 9 mm. In still another example, an average cross linked band grip force of the ligation band is at least about 0.50 N. The elastic body can also be synthetic polyisoprene.

In another aspect, a method of ligating tissue is provided including drawing tissue into an inner lumen of an elongate shaft. The method also includes advancing a ligation band distally along the elongate shaft and distally off of a distal end of the elongate shaft to position the ligation band around the tissue drawn into the inner lumen of the elongate shaft. The ligation band has a plurality of protrusions formed on first and second opposed tissue-contacting surfaces thereof that grip the enclosed tissue to resist slipping. The plurality of protrusions can define an interlinking web-pattern with a plurality of recesses therebetween that receive the tissue therein.

The method can have numerous variations. For example, the band can apply a compressive force of at least about 5.5 N when expanded to 7.5 mm. In another example, the band can apply a compressive force of at least about 6.5 N when expanded to 9 mm.

The method can also include, prior to drawing tissue into the inner lumen, loading a plurality of ligation bands onto a distal portion of the elongate shaft. In another example, advancing the ligation band along the elongate shaft can include pulling cords proximally through the inner lumen of the elongate shaft to cause beads arranged on distal portions of the cords to move distally along an outer surface of the elongate shaft. In such an example, the cords can extend distally through the inner lumen of the elongate shaft, wrap around the distal end of the elongate shaft, and extend proximally along the outer surface of the elongate shaft.

BRIEF DESCRIPTION OF THE DRAWINGS

This invention will be more fully understood from the following detailed description taken in conjunction with the accompanying drawings, in which.

DETAILED DESCRIPTION

Figure 1A:
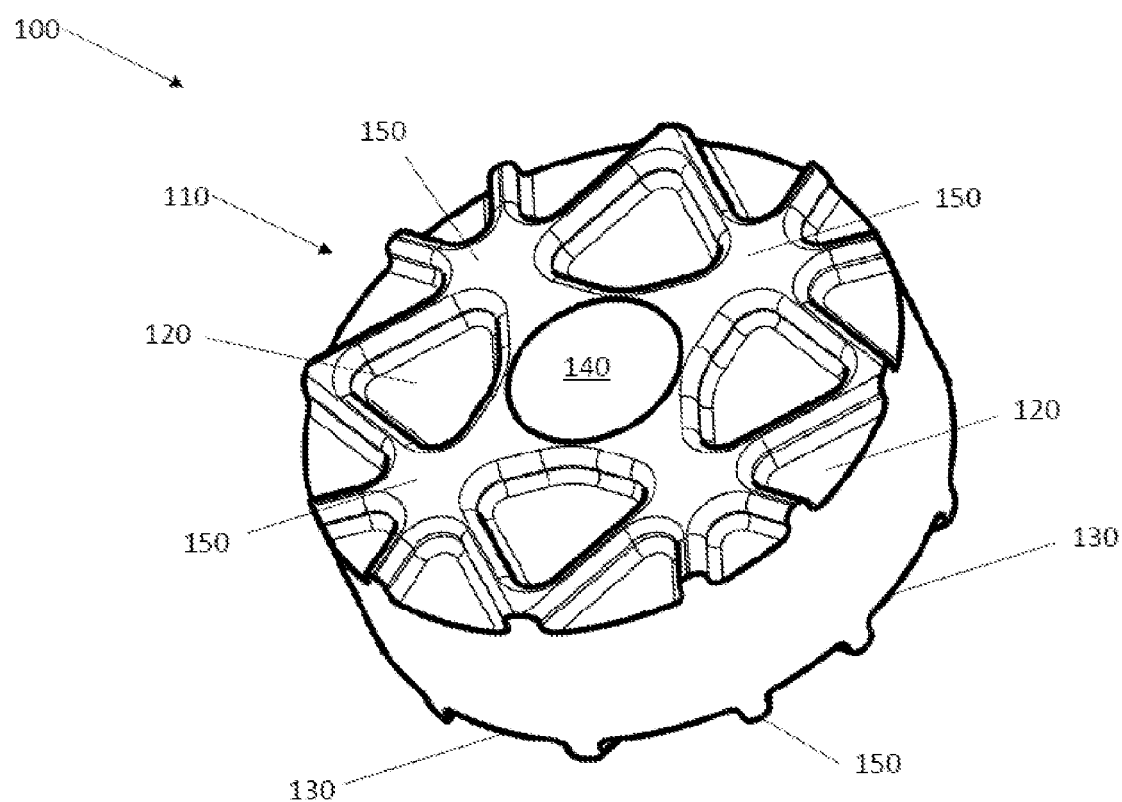
FIG. 1A is perspective view of one exemplary embodiment of a ligation band.

Certain exemplary embodiments will now be described to provide an overall understanding of the principles of the structure, function, manufacture, and use of the ligation bands and methods disclosed herein. One or more examples of these embodiments are illustrated in the accompanying drawings. Those skilled in the art will understand that the ligation bands and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed ligation bands and methods, such dimensions are not intended to limit the types of shapes that can be used in conjunction with such ligation and methods. A person skilled in the art will recognize that an equivalent to such linear and circular dimensions can easily be determined for any geometric shape. Sizes and shapes of the ligation bands, and the components thereof, can depend at least on the anatomy of the subject in which the ligation bands will be used, the size and shape of components with which the ligation bands will be used, and the methods and procedures in which the ligation bands will be used.

In general, ligation bands are provided having tissue-gripping features that resist slipping or releasing tissue once applied. The tissue-gripping features are designed to add resistance to stretching of each band, both during loading of the band onto a delivery device to create greater delivery energy when applied to tissue and after being applied to tissue to create increased friction against the constricted tissue while reducing band slippage. The tissue-gripping features thus prevent or reduce the likelihood of constricted or trapped tissue, called a pseudopolyp, from slipping through the band. Reducing band slippage results in much safer procedures because band slippage is a significant complication in band ligation, both during the procedure and at a later point. Even after the procedure is completed and bands initially seem to hold and create a satisfactory pseudopolyp, one or more bands can slip, resulting in bleeding and causing increased complications because a patient is no longer with a surgeon. Thus, the tissue-gripping features can reduce both immediate band slippage and delayed band slippage.

In an exemplary embodiment, a ligation band is provided having a substantially ring-shaped molded body with a first tissue-contacting surface and a second tissue-contacting surface that is opposite the first tissue-contacting surfaces. The molded body can have a central opening or aperture extending therethrough between the first and second tissue-contacting surfaces. The first and/or second tissue-contacting surfaces can include tissue-gripping features thereon. In one embodiment, the tissue-gripping features can be in the form of protruding surface features, such as raised ridges, in predetermined patterns or shapes and defining recesses therebetween. The pattern can add resistance to stretching of the band and assist in returning a band to its original resting shape with as little deformation as possible, providing greater constrictive gripping force. The pattern can also create additional friction between constructed tissue and the first and second tissue-contacting surfaces to reduce or prevent entirely the constricted tissue from slipping through the central opening or aperture of the band. The pattern can allow tissue to extend into the recesses to assist in providing enhancing anti-slip properties. Thus, the ligation band can be configured to have enhanced elasticity, and therefore greater retention ability, as compared to conventional ligation bands so as to provide enhanced compression.

Figure 1B:
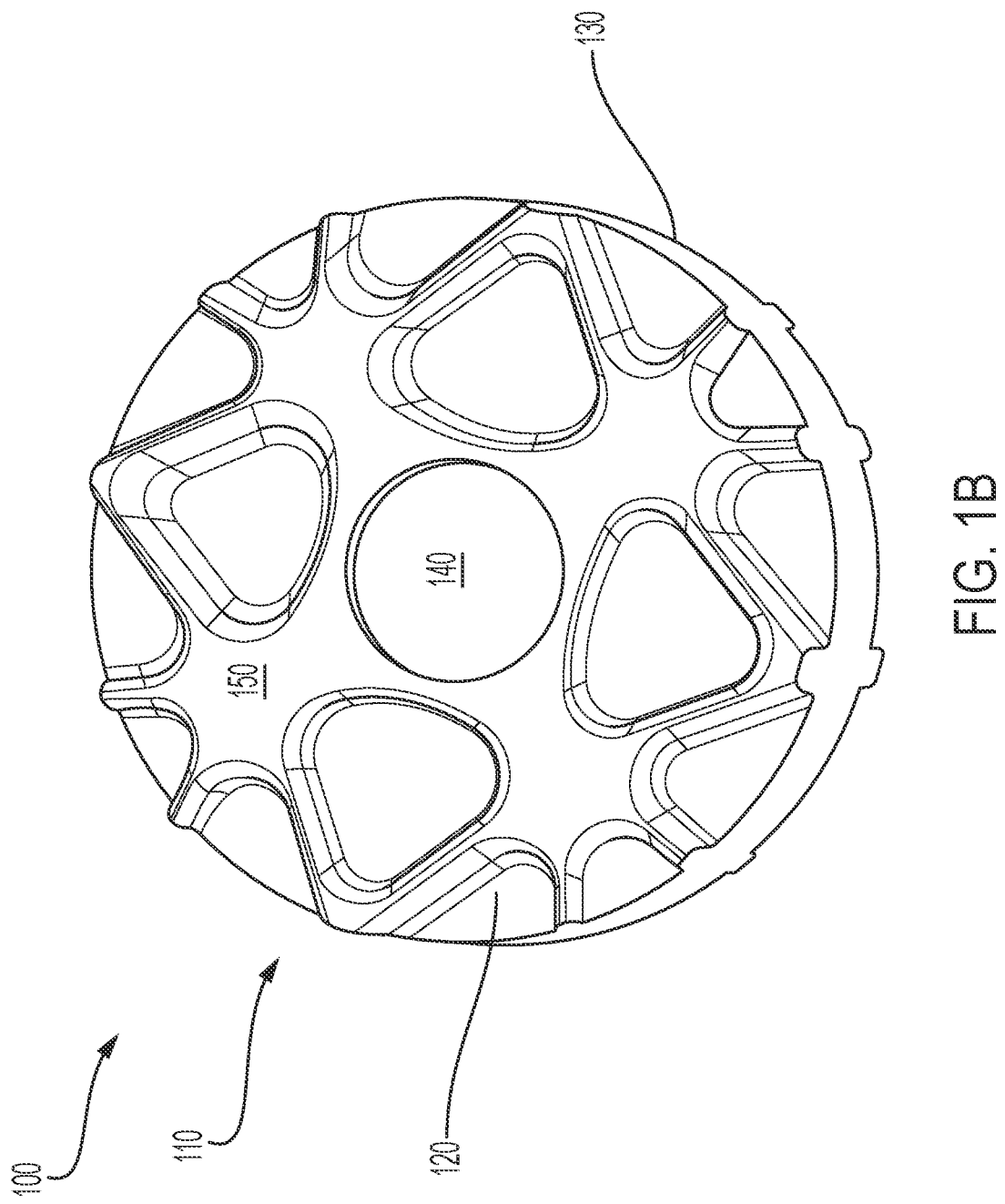
FIG. 1B is a top-down view of the ligation band of FIG. 1.
Figure 1C:
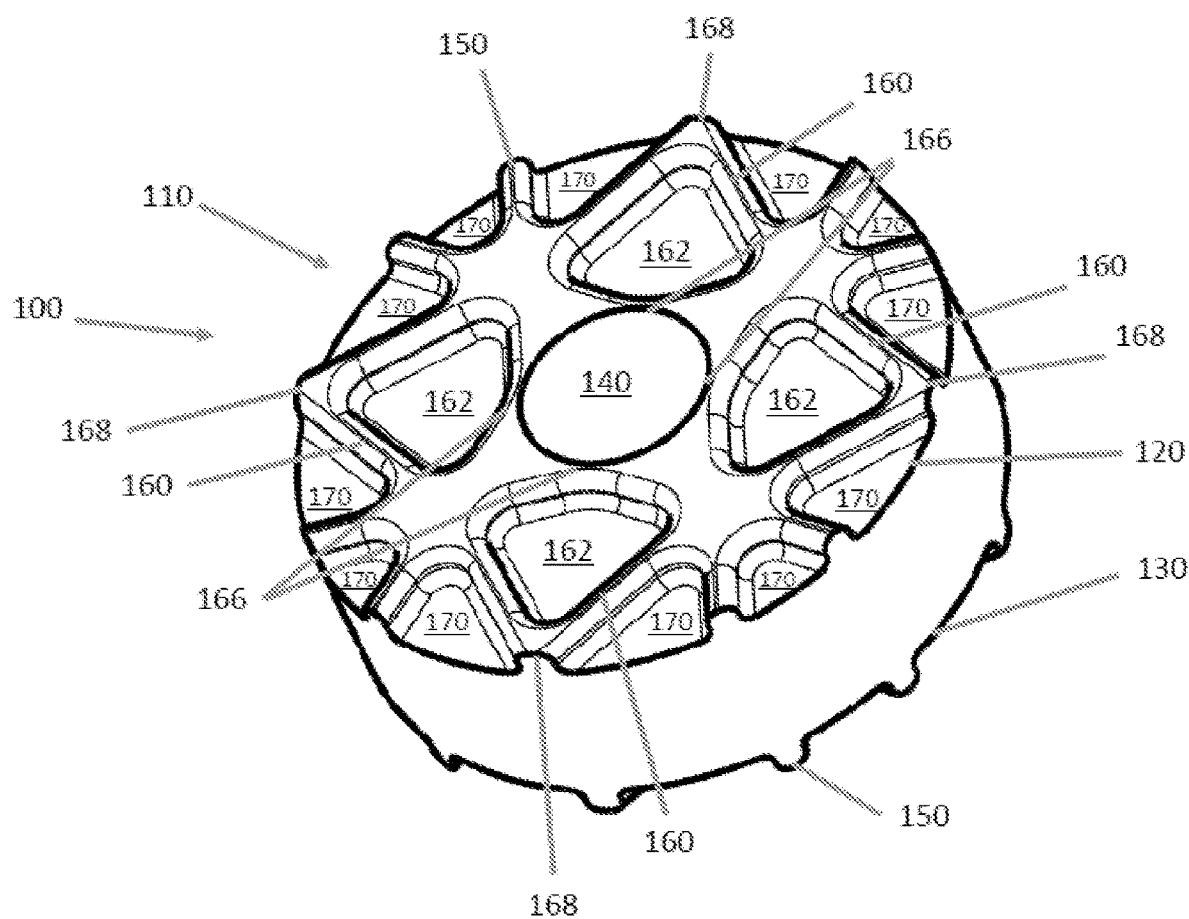
FIG. 1C is a perspective view of the ligation band of FIG. 1.

FIGS. 1A-1C illustrate one exemplary ligation band 100 having a body 110. While the ligation band can have a variety of shapes and sizes, the ligation band 100 in FIGS. 1A-1C has a substantially circular or ring shape with inner and outer diameters. The body 110 can be molded from any suitable material, such as various elastics, polymers, isomeric material(s), blends of synthetic polyisoprene, etc.

As shown in FIGS. 1A-1C, the body 110 has a first tissue-contacting surface 120 and a second tissue-contacting surface 130. The body 110 also has a central aperture 140 extending through the first and second tissue contacting surfaces 120, 130. The aperture 140 defines the inner diameter of the ligation band 100. In this illustrated embodiment, both the first and second tissue-contacting surfaces 120, 130 include tissue-gripping features 150 thereon that create uneven or friction-inducing anti-slip surfaces. In other embodiments, any portion of either the first tissue-contacting surface 120 or the second tissue-contacting surfaces 130 can include tissue-gripping features 150 or the surfaces 120, 130 can have different tissue-gripping features 150 formed thereon.

While the tissue-gripping features 150 can have a variety of configurations, the tissue-gripping features 150 shown in FIGS. 1A-1C are in the form of surface features or protrusions defining an interlocking web-like pattern with a plurality of recesses therebetween. The tissue-gripping features 150 can act as a superstructure or a buttressing design to add resistance to stretching of the band 100 as it is loaded onto a delivery device, for example by being stretched over a delivery barrel. The increased resistance to stretching caused by the tissue-gripping features 150 can create a greater delivery force upon being applied to tissue. This delivery force can be the result of transferring static or potential energy to kinetic energy when the band is released from the delivery device and allowed to return to its original resting diameter. The tissue-gripping features 150 can also assist in pulling the band back into its original shape upon delivery with as little deformation as possible, creating a secure constriction on any tissue therein. In addition to the force of delivery and constriction, the tissue-gripping features 150 also create additional friction between the tissue-contacting surfaces 120, 130 and the tissue, preventing or greatly reduce slippage while also not being on surfaces that are overly sensitive to damage or bleeding.

Figure 1D:
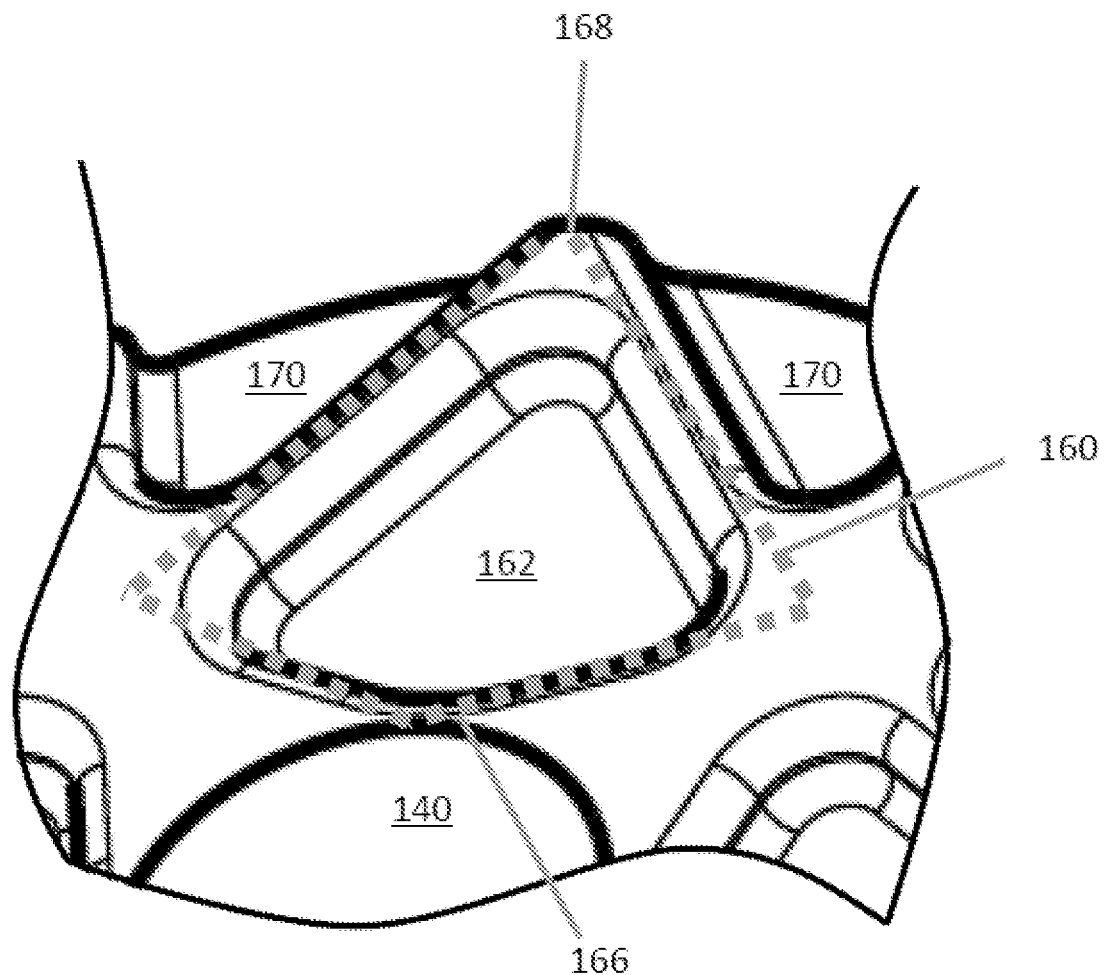
FIG. 1D is an enlarged perspective view of a delta-shaped structure on the ligation band of FIG. 1.
Figure 1E:
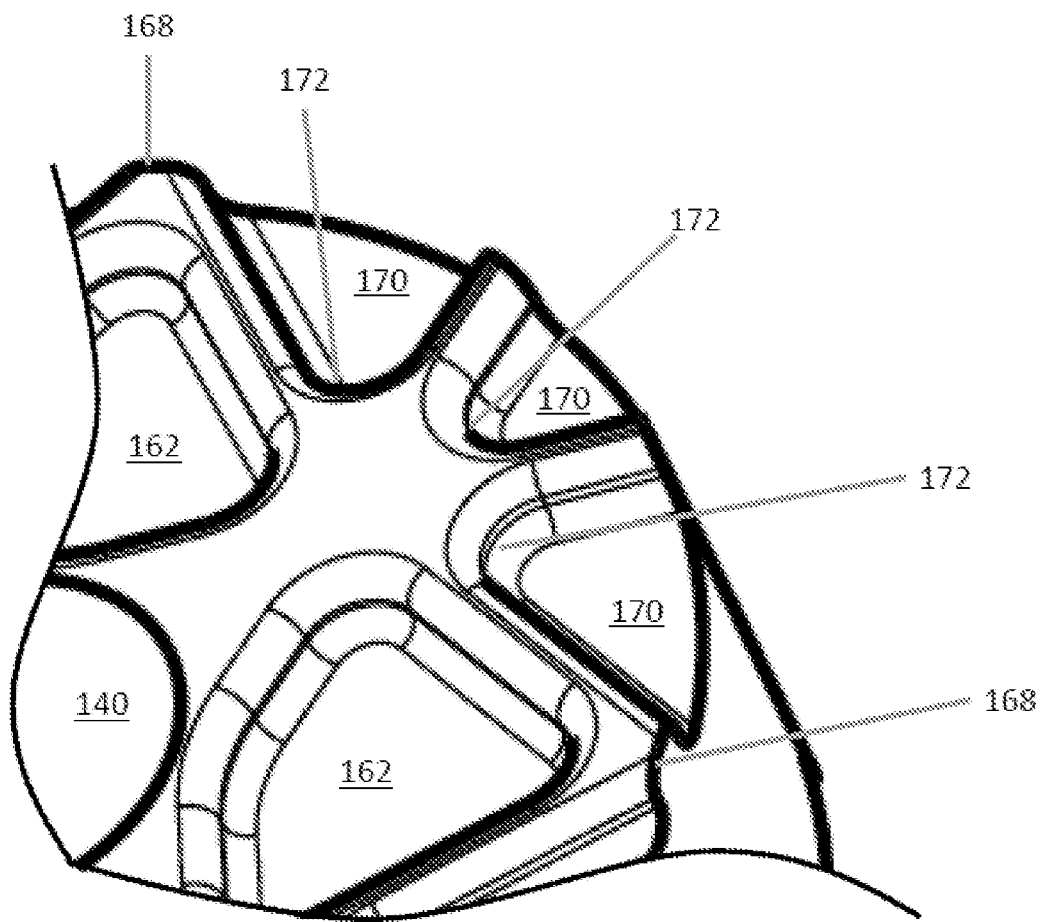
FIG. 1E is an enlarged perspective view of a group of recesses on the ligation band of FIG. 1.

In the illustrated embodiment, the tissue-gripping features 150 provide an interconnected or cross-linking pattern of ridges having delta-like structures defining triangular recesses therein, however other shapes and configurations are possible, such as circles, squares, rectangles, stripes, checkered or interlocking grid configurations, etc. The pattern, such as the delta-like shapes, can be specifically selected to provide additional resistance to stretching and deformation and to provide increased friction between the surfaces 120, 130 and any tissue gripped therein. FIGS. 1A-1C illustrate four delta-shaped structures 160 formed by ridges projecting above the tissue-contacting surface 120 and defining four corresponding delta-shaped recesses 162 spaced equidistant around the central aperture 140. Each delta-shaped structure 160 has one side 166 that faces the aperture 140, such that the delta-shaped structure 160 has an apex 168 that is oriented away from the central aperture 140. The side 166 positioned closest to the central aperture 140 can have a slight curvature or bend formed therein, as shown. FIG. 1D shows an enlarged delta-shaped structure 160 from FIGS. 1A-1C with broken lines tracing an approximate shape of the delta-shaped structure 160. Additional recesses 170 (i.e., perimeter recesses) are positioned around the perimeter, with three perimeter recesses 170 being formed between two adjacent apexes 168 of two adjacent delta-shaped structures 160. The perimeter recesses 170 can have the shape of a portion of a delta or triangle, with a recess apex 172 pointing inward toward the central aperture 140. Each perimeter recess can vary in size. In the illustrated embodiment, for each set of three perimeter recesses, a central perimeter recess is smaller in size than the adjacent recesses. FIG. 1E shows an enlarged group of three perimeter recesses 170 from FIGS. 1A-1C, positioned between two adjacent apexes 168 of two adjacent delta-shaped structures 160 with each corresponding recess apex 172 identified.

The central aperture 140 can also have a variety of configurations, but in an exemplary embodiment it is substantially cylindrical. An inner sidewall of the aperture 140 can be smooth, as illustrated in FIGS. 1A-1C, with no surface features formed thereon. The aperture 140 captures tissue that can be thin, vulnerable, and prone to excessive bleeding. As such, the smooth inner surface of the aperture 140 can avoid any abrasions or uneven pressure being applied to the sensitive tissue to create safer ligation.

The band can be molded using a variety of techniques. For example, in some embodiments, the band can be injection molded. In one embodiment, the band can be manufactured by injection molding one or more elastics, polymers, isomeric material(s), blends of synthetic polyisoprene, etc. Further, the band 100 can be latex-free, discussed further below with reference to sample test results.

Figure 2:
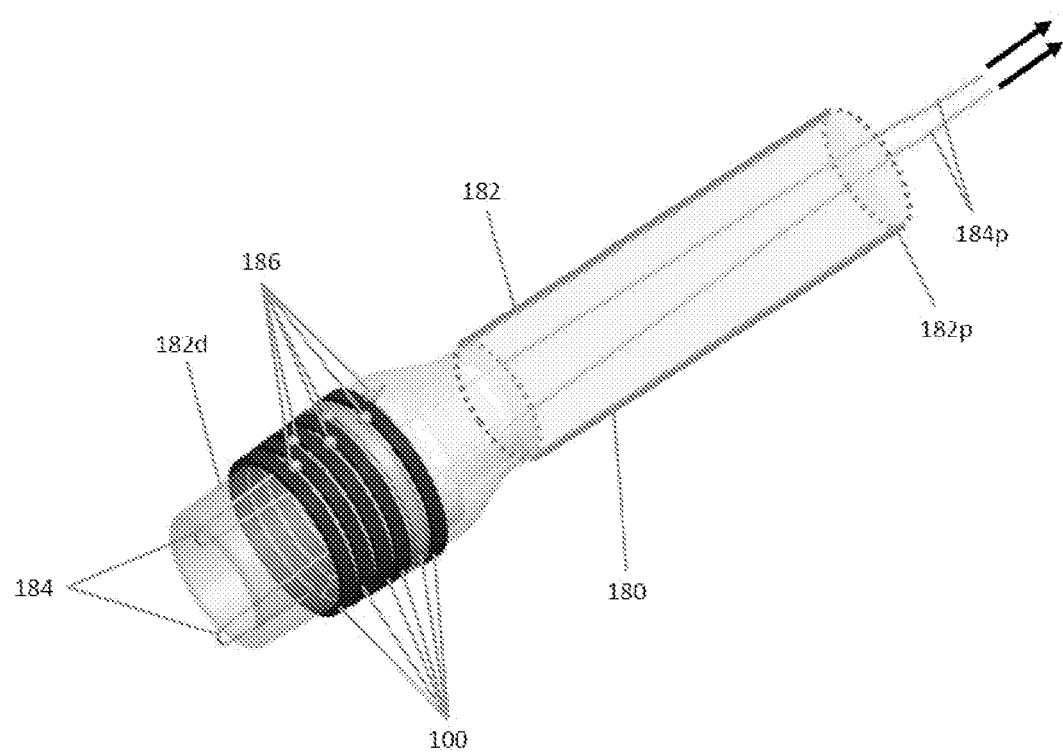
FIG. 2 is a perspective, partially-transparent view of a plurality of the ligation bands of FIG. 1 on a delivery device.

In use, one or more ligation bands 100 can be loaded onto a delivery device 180, as illustrated in FIG. 2. The band 100 can be moved from a contracted or initial resting state to a stretched or deployment state by placing the ligation band 100 around a distal end or head 182d of a delivery barrel 182 of the delivery device 180 such that the barrel 182 extends through the aperture 140 of the ligation band 100. The barrel 180 can be used to deploy the ligation band 100 around tissue, such as a variceal channel. For example, the barrel 180 can suction tissue into a distal opening of the distal end 182d thereof, and the ligation band 100 can be advanced distally along an outer surface of the barrel 182 and released from the distal end 182d of the barrel 182 to position the band 100 around the tissue suctioned into the distal end 182d.

The band 100 can be released from the barrel 182 using various mechanisms, such as a cord 184 and bead 186 combination illustrated in FIG. 2. During initial placement and loading of the band 100 on the distal end 182d, cords 184 can be extended down the barrel 182, passed out the distal opening of the distal end 182d, and pulled back along the outer surface of the distal end 182d. A proximal end 184p of each cord 184 can extend proximally out of a proximal end 182p of the barrel 182. Beads 186 can be fixed at various points along the cords 184, and each loaded band 100 can be placed on the barrel 182 distally in front of a corresponding bead 186 on each cord 184. To advance the band 100 distally along the outer surface of the barrel 182 to cause deployment, the proximal ends 184p of the cords 184 can be pulled proximally, as indicated by arrows in FIG. 2. The cords 184 extend distally through the barrel 184 and then wrap around the distal end 182d of the barrel 182 to extend proximally along the outer surface of the barrel 182. As such, pulling the proximal ends 184p of the cords 184 proximally causes distal segments of the cords 184 on the outer surface of the barrel 182 to get pulled distally initially toward the distal end 182. When they reach the distal end 182d, they rotate around the distal end 182d into the distal opening of the barrel 182 and get pulled proximally through the barrel 184. The beads 186 on the cords 184 will get pulled distally toward the distal opening of the barrel 182 with the distal segments of cords 184, and each band 100 positioned distally in front of the corresponding bead(s) 186 will also get pulled distally toward the distal opening of the barrel 182. As the beads 186 reach the distal opening of the barrel 182, they will rotate around the distal end 182d and be pulled into the distal opening of the barrel 182 to then move proximally through the barrel 182 with the cords 184. However, the corresponding band 100 will pop off the distal end 182d of the barrel 182 when the corresponding bead(s) 186 rotate into the barrel 182, and the band 100 is thus deployed from the barrel 182 to close on any tissue suctioned into the distal opening of the barrel 182 at that time, as described in PCT Application WO/2016/086003, filed Nov. 24, 2015, and U.S. Provisional Patent App. No. 62/085,272, filed on Nov. 27, 2014, both of which are incorporated by reference herein. As the ligation band 100 is deployed around tissue, it contracts from the stretched deployment state to a contracted or initial resting state in which the band 100 engages the tissue.

Given the elastomeric properties of the ligation band 100, when in a tissue deployment state, the ligation band 100 traps tissue therein (e.g., within the aperture 140 of the ligation band 100) by exerting a compressive force to the tissue thereby resulting in ligation of the tissue. This compressive force also promotes healing of the tissue. Once the ligation band 100 is deployed around tissue, tissue adjacent to the tissue within the aperture 140 can come into contact with the first and second tissue contacting surfaces 120, 130. As such, the tissue-gripping features 150 of the ligation band 100 will engage the tissue to thereby further promote band retention at the treatment site (e.g., substantially prevent band slippage). For example, the tissue-gripping features 150 can cause the adjacent tissue to be trapped within the recesses defined by the tissue-gripping features 150 thereby preventing slippage. Band retention and preventing slipping thus avoid a failed ligation treatment and excessive bleeding.

The ligation band 100 can be stretched from the initial resting state to the initial deployment state by a significant degree. In some aspects, the ligation band 100 can have an elongation ratio of 750%, meaning that the ligation band 100 can be stretched up to 7.5 times its initial resting inner diameter.

The present teachings may be further understood with reference to the following non-limiting examples.

EXAMPLES

Example 1: Compression Force

Sample batches of various ligation bands were placed on a barrel. Batch 1 are exemplary ligation bands configured in accordance with the present disclosure, whereas the remaining batches 2-4 are conventional bands (Batch 2 is Smart-Band latex from Intelligent Endocopy; Batch 3 is Six Shooter Bands from Cook Medical; and Batch 4 is Speedband Superview Super 7 from Boston Scientific).

Prior to testing the compression force of each band at various band expansions, the bands were removed from the barrel and immediately pre-conditioned in a 37° C.±2° C. water bath for 30 seconds. The water bath was a beaker filled with water and heated in the lab oven. The temperature was measured to ensure 37° C.±2° C. before each sample. A heat lamp attached to a temperature controller was installed to ensure a test temperature of 37° C.±2° C.

One half of the fixture was mounted to the base of a tensile tester and one half to a load cell. The two halves were separated by a minimum gap; this setup corresponds to 2 mm tissue diameter Immediately after preconditioning, the band was slipped over the two semi-circular pins (each 0.080"/2 mm wide) on the fixture and the test was started.

After 2 minutes in the initial position, the load cell moved to the next position with a speed of 50 mm/min. The force was measured for 2 minutes and so on, until compression forces were measured in all positions. Load cell displacements equivalent to the test diameters are listed in Table 1 below. The load cell displacement (column B) is the fixture gap that corresponds to an inner perimeter of the stretched band that equates to a band that would be stretched to the expanded ID (column A).

TABLE 1

| Column A<br>Band expanded ID [mm] | Column B<br>Load cell displacement [mm] |
|---|---|
| 2.0 | 0 |
| 3.0 | 1.5 |
| 4.5 | 3.9 |
| 6.0 | 6.2 |
| 7.5 | 8.6 |
| 9.0 | 10.9 |

The measured compression forces were recorded. The compression force averages (CF) and standard deviation (Std) per band expansion group and sample batch is shown in Table 2 below and graphically in FIG. 3, in which "n" represents a position of the tested band on a barrel.

TABLE 2

| Batch No. | "n" | 2 mm band expansion | | 3 mm band expansion | | 4.5 mm band expansion | | 6 mm band expansion | | 7.5 mm band expansion | | 9 mm band expansion | |
|---|---|---|---|---|---|---|---|---|---|---|---|---|---|
| | | CF [N] | Std | CF [N] | Std | CF [N] | Std | CF [N] | Std | CF [N] | Std | CF [N] | Std |
| Batch 1 | 10 | 0.00 | 0.004 | 1.54 | 0.109 | 3.35 | 0.225 | 4.81 | 0.351 | 6.25 | 0.470 | 7.62 | 0.586 |
| | 8 | 0.00 | 0.004 | 1.57 | 0.090 | 3.43 | 0.164 | 4.94 | 0.246 | 6.43 | 0.320 | 7.85 | 0.394 |
| | 2 | 0.00 | 0.000 | 1.40 | 0.009 | 3.02 | 0.053 | 4.29 | 0.075 | 5.54 | 0.104 | 6.73 | 0.164 |
| Batch 2 | 10 | 0.19 | 0.052 | 1.67 | 0.082 | 3.11 | 0.220 | 4.19 | 0.325 | 5.22 | 0.437 | 6.11 | 0.525 |
| | 8 | 0.17 | 0.015 | 1.69 | 0.064 | 3.19 | 0.138 | 4.32 | 0.186 | 5.40 | 0.226 | 6.33 | 0.267 |
| | 2 | 0.28 | 0.014 | 1.56 | 0.061 | 2.76 | 0.079 | 3.66 | 0.077 | 4.48 | 0.045 | 5.21 | 0.004 |
| Batch 3 | 10 | 0.17 | 0.134 | 1.39 | 0.204 | 2.59 | 0.299 | 3.49 | 0.387 | 4.35 | 0.473 | 5.09 | 0.529 |
| Batch 4 | 7 | 0.01 | 0.029 | 1.38 | 0.068 | 2.94 | 0.117 | 4.13 | 0.172 | 5.26 | 0.239 | 6.31 | 0.312 |

Figure 3:
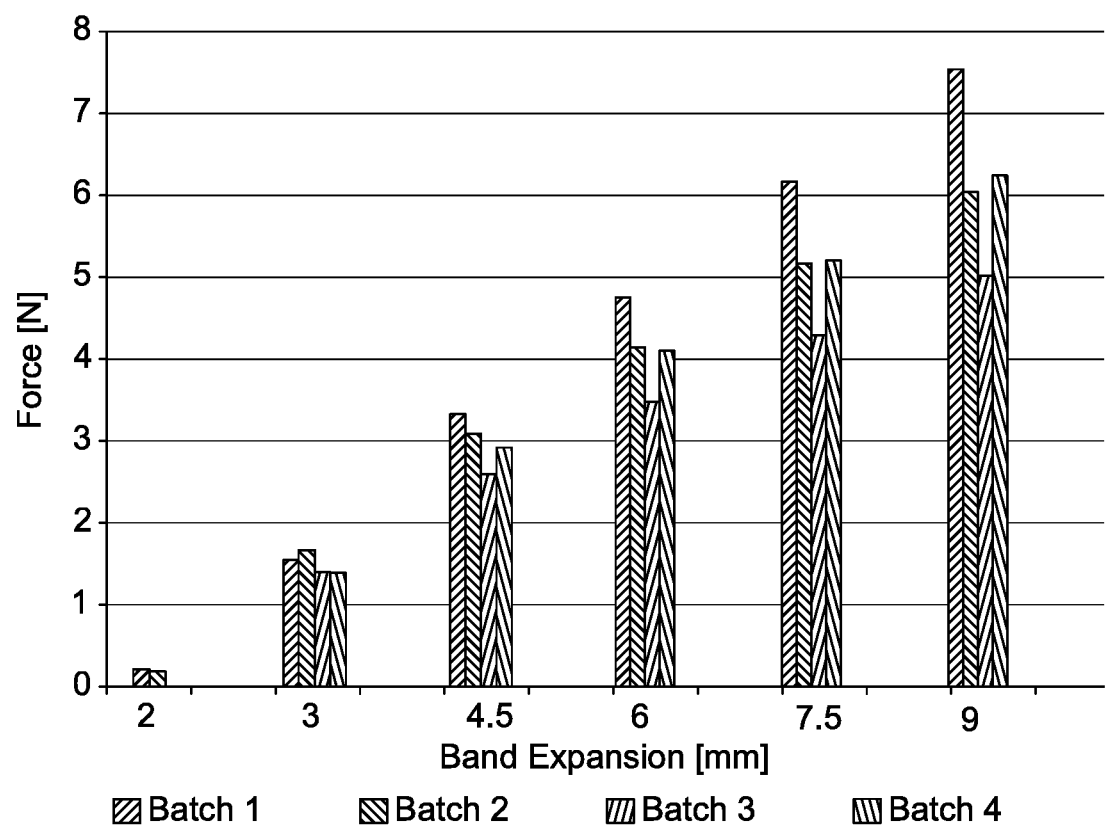
FIG. 3 is a graph illustrating Force [N] v. Band Expansion [mm] of the ligation bands in Example 2.

As shown in Table 2 and FIG. 3, the exemplary ligation bands of the present disclosure (Batch 1) have a consistent compression force that is at least about 25% greater than that of the remaining tested bands (Batches 2-4) at a 9 mm band expansion. For example, at 6 mm, a compressive force of the bands of the present application in Batch 1 ranged from 4.29 N to 4.94 N compared to the next best performing bands in Batch 2 of 3.66 N to 4.32 N. This results in an average compressive force of the bands of the present application of 4.68 N compared to an average of 4.06 N of Batch 2, resulting in an over 15% increase in compressive force over the best alternative band. At 7.5 mm expansion, the compressive force of the bands of the present application in Batch 1 outperformed every other band in every test, ranging from 5.54 N to 6.43 N compared to the next best performing bands in Batch 2 of 4.48 N to 5.40 N. This results in an average compressive force of the bands of the present application of 6.07 N compared to an average of 5.03 N of Batch 2, resulting in an over 20% increase in compressive force over the best alternative band. At 9 mm expansion, the compressive force of the bands of the present application in Batch 1 outperformed every other band in every test again, ranging from 6.73 N to 7.85 N compared to the next best performing bands in Batch 2 of 5.21 N to 6.33 N. This results in an average compressive force of the bands of the present application of 7.4 N compared to an average of 5.88 N of Batch 2, resulting in an over 25% increase in compressive force over the best alternative band.

The tested bands in Batch 1 are also latex free. Latex can have a beneficial stretch ratio and/or a beneficial ability to return to its original shape and elasticity, and thus it is a common material to be used in ligation bands. For example, natural rubber latex can be stretched repeatedly to seven or eight times its original length and can return to its original shape. It also reacts to higher temperatures (such as temperatures in the human body) to shrink back to its original shape when applied to tissue for ligation. However, hospitals and other surgical spaces prefer to avoid latex due to latex allergies. Batches 1 and 3 are each latex-free bands, while Batches 2 and 4 are latex bands. The test results thus show that, not only do the bands provided herein and represented in Batch 1 close the performance gap between latex and non-latex bands, but the latex free bands in Batch 1 outperform current latex bands. The other latex free bands tested in Batch 3 performed the worst of the tested bands, and thus surgeons may have been inclined to use latex bands (even knowing allergies may cause issues) to achieve better band performance. However, the latex free bands of Batch 1 perform as good as or better than latex bands in Batches 2 and 4, and especially in the 4.5 mm to 7.5 mm band expansion range that represents an exemplary diameter of a variceal bleeding pseudopolyp. The bands of the present application, as shown by the results in Batch 1, thus allow surgeons to achieve better performance while also avoiding latex and any complications caused by latex allergies.

The bands in Batch 1 can be made from synthetic polyisoprene, which avoids using latex but can have some limitations such as in some cases not being as elastic as latex. However, the tissue-gripping features on the bands of Batch 1, such as the delta-shaped structures and recesses discussed above, can provide bands with better band retention and/or the ability to return to its original resting diameter once deployed from a deployment barrel while also being made of latex-free material. Synthetic polyisoprene and/or synthetic latex free rubber can have a same basic chemical formula as natural rubber latex, however due to its properties, it can be injection molded to produce shapes and forms incorporated into a band design that may be more difficult and/or time consuming to produce with natural latex. Molding latex free synthetic polyisoprene is very controlled and is formed by a precise and controlled chemical process, unlike natural latex. Previously, however, the stretch ratio and/or the elasticity or ability to return to a band's original resting inner diameter of natural latex bands resulted in the latex bands outperforming non-latex bands, such as shown in Batches 2 and 4 versus Batch 3 above. Elastic properties of latex (or modulus or stretch ratio) can in some cases be typically about 10-15% more effective than those of synthetic polyisoprene. As such, if latex bands and non-latex bands were compared that were otherwise identical except for the material (identically-shaped bands loaded onto an endoscopic banding kit with the same inner diameter and same thickness and dimensions), a surgeon might assume that the latex bands would provide about a 10 to 15% on average better compression force to a treatment site. Aside from a risk of a latex allergy, a patient would have less chance of a band slippage event leading to a re-bleed after treatment. Thus, latex bands were preferred. However, the tissue-gripping features on the bands of Batch 1, such as the delta-shaped structures and recesses discussed above, can provide as good or better performance than the latex bands while being latex free.

Example 2: Band Grip (Anti-Slip) Properties

Figure 4B:
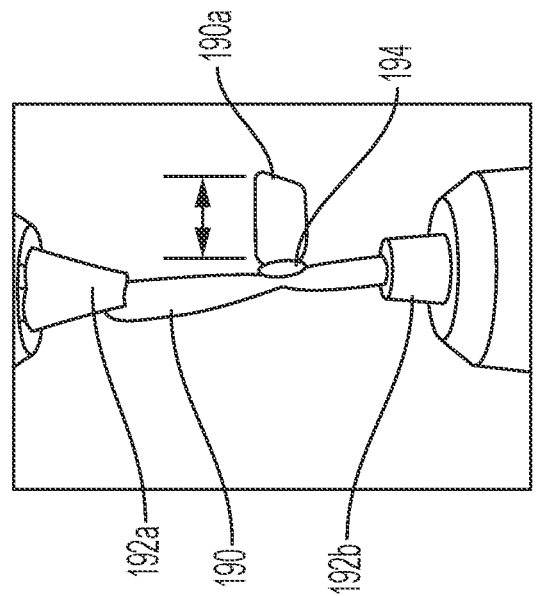
FIG. 4B is a perspective view of an exemplary test setup used during Example 3.
Figure 4A:
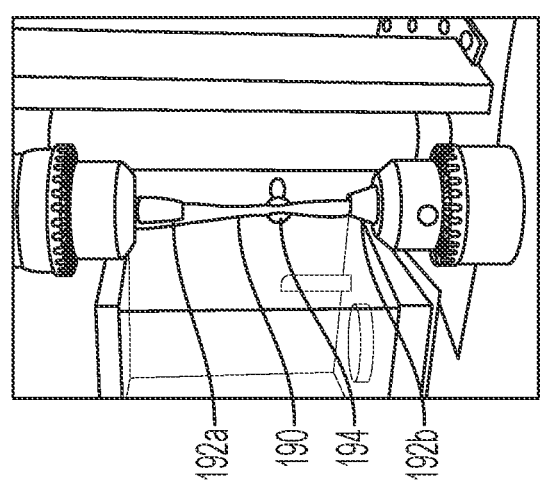
FIG. 4A is a perspective view of an exemplary test setup used during Example 3.

Two sets of six ligation bands were tested for their gripping (slipping) behaviors using a balloon as tissue imitation. The first set included six sample ligation bands made in accordance with the present disclosure (IE bands), and the second set included six Speedband Superview Super 7 bands from Boston Scientific (BSC bands). FIGS. 4A and 4B illustrate an exemplary setup for the test. For each band test, each end of a balloon 190 (simulating tissue) was fastened in a pin chuck 192a, 192b. One pin chuck was attached to the load cell and one to the base of the tensile tester. The gauge length between the pin chucks was adjusted to 15 mm A band 194 was shot onto a folded section 190a of the balloon 190 leaving a balloon fold of approximately 20 mm. The pin chucks 192a, 192b were separated by a speed of 100 mm/min until the band 194 snapped off the balloon 190.

Figure 5:
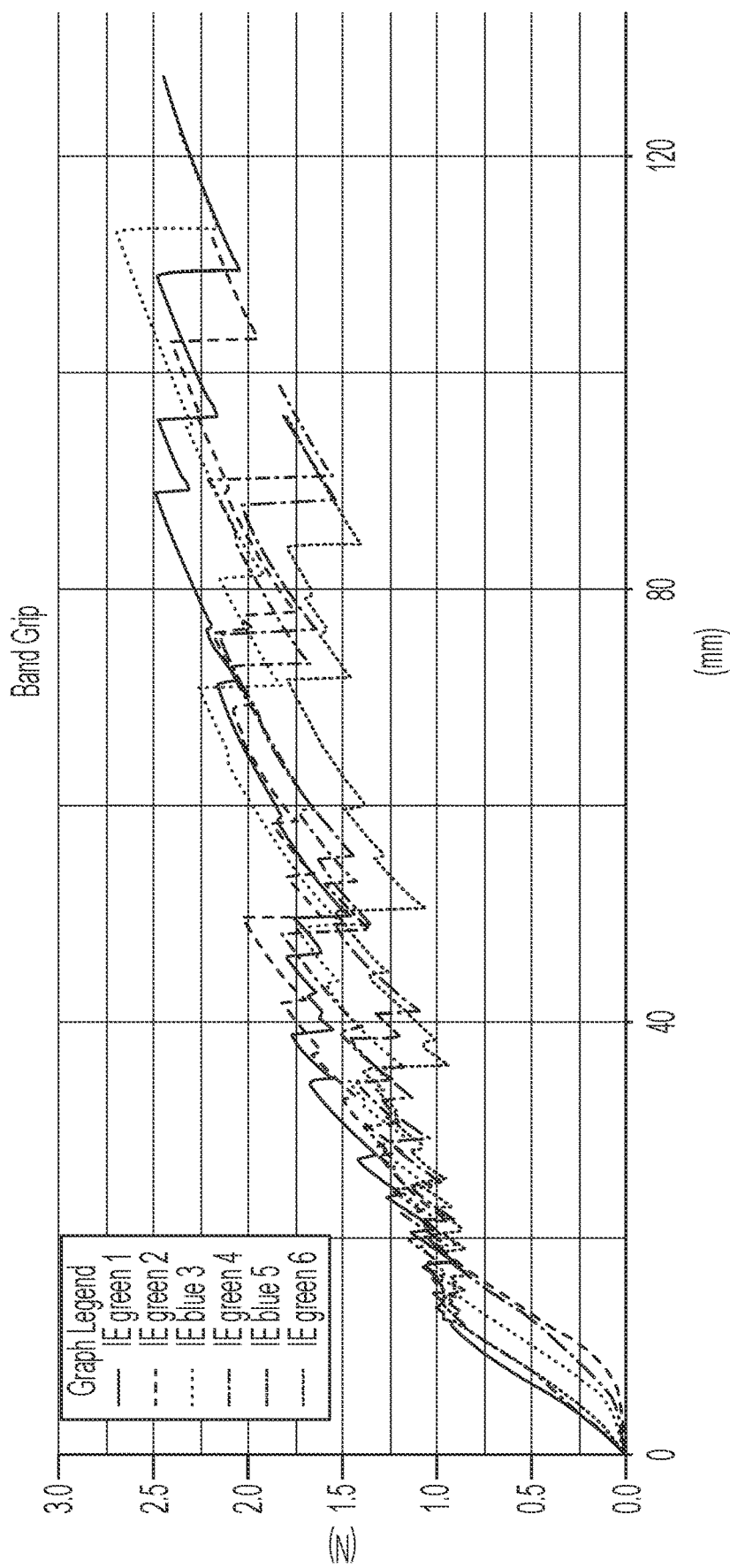
FIG. 5 is a graph illustrating the band grip results of the bands in Example 3.
Figure 6:
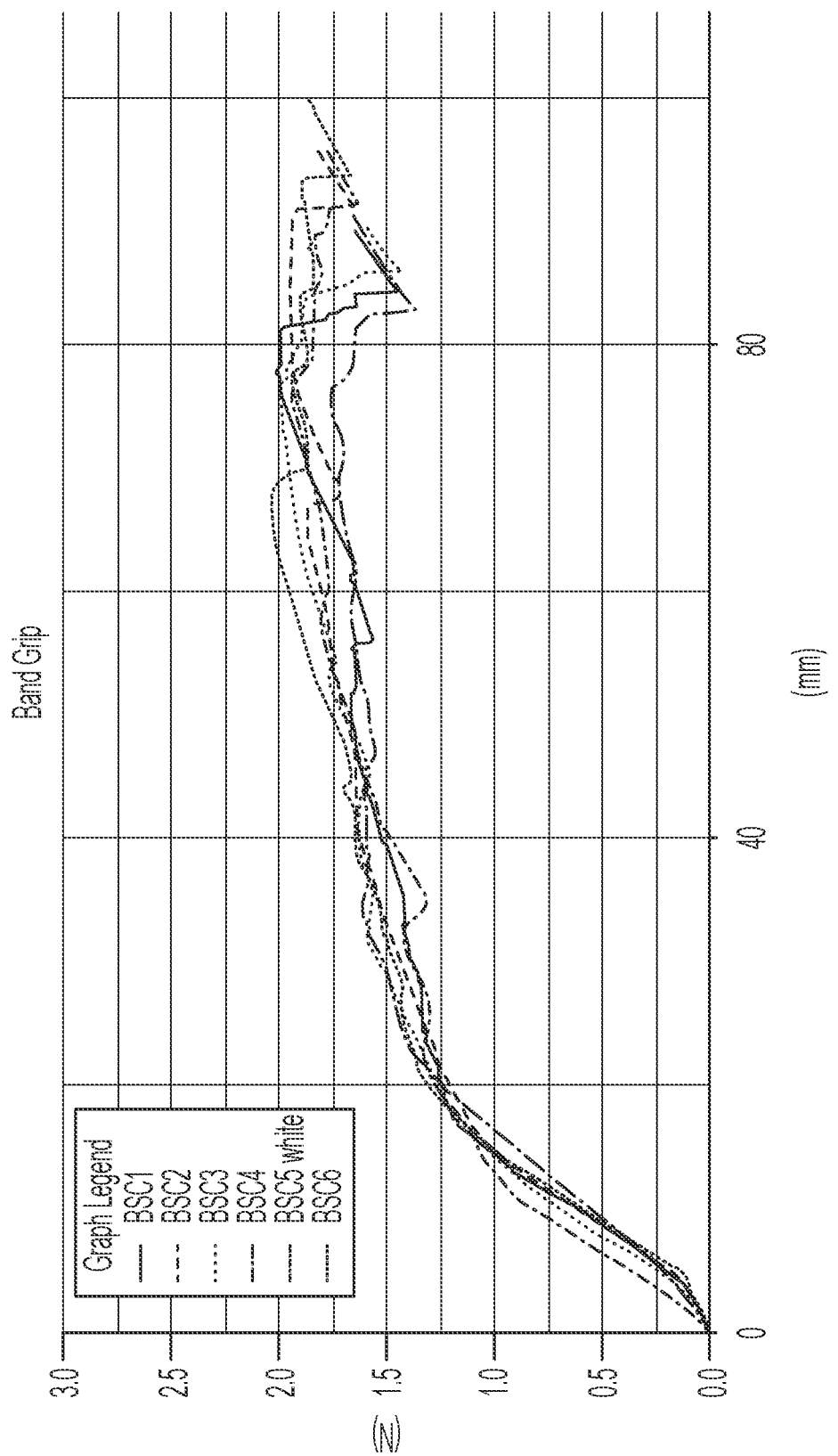
FIG. 6 is a graph illustrating the band grip results of the bands in Example 3.

The displacement force for each IE band is graphically illustrated in FIG. 5 and the displacement force for each BSC band set is graphically illustrated in FIG. 6. The graphs show that the IE bands have an intermittent slipping followed by gripping behavior while the BSC bands slip more steadily. This can be seen as the "saw-tooth" or "jagged" line pattern in the IE graph compared to the smoother line of the BSC graph.

Table 4 below summarizes values for the maximum force achieved before final band slip-off (final peak) and the minimum force after final slip-off (valley after final peak). The cross linked band grip force is represented by the force drop and is determined by subtracting the minimum force from the maximum force at final slip-off. The minimum force represents the force contributed by the stretching balloon.

TABLE 4

| Band | Position on Barrel | Max. Force achieved before slipping off [N] | Min. Force after slipping off (balloon stretch Force) [N] | Force Drop (Max − Min) [N] |
| --- | --- | --- | --- | --- |
| IE green 1 | 3 | 2.49 | 2.04 | 0.45 |
| IE green 2 | 4 | 2.40 | 1.94 | 0.47 |
| IE blue 3 | 5 | 2.69 | 1.91 | 0.78 |
| IE green 4 | 6 | 2.15 | 1.53 | 0.62 |
| IE blue 5 | 5 | 2.19 | 1.56 | 0.63 |
| IE green 6 | 6 | 1.80 | 1.38 | 0.42 |
| Averages | | 2.29 | 1.73 | 0.56 |
| BSC blue 1 | 2 | 2.01 | 1.44 | 0.57 |
| BSC blue 2 | 3 | 1.95 | 1.65 | 0.30 |
| BSC blue 3 | 4 | 2.00 | 1.43 | 0.57 |
| BSC blue 4 | 5 | 1.76 | 1.37 | 0.39 |
| BSC white 5 | 6 | 1.94 | 1.62 | 0.32 |
| BSC blue 6 | 7 | 2.03 | 1.67 | 0.36 |
| Averages | | 1.95 | 1.53 | 0.42 |

Thus, when BSC bands are ligated onto silicone balloons during testing, the bands attempt to grab onto the silicone material (simulating tissue) with round and smooth surfaces. The surface of the band and the surface of the silicone balloon are thus similar to each other and provide minimal grabbing ability. As the intron machine starts to pull on the balloon material from the sides to pull the silicone balloon out of the bands, the smooth surface of the BSC band does a poor job of gripping onto the silicone balloon (simulating tissue) when compared to the IE bands.

As shown in Table 4, the IE bands achieve higher forces, i.e. grip longer than the BSC bands. The average maximum cross linked grip force of the IE bands during this test was approximately 33% higher (0.42 N versus 0.56 N) than the BSC bands. The 0.56 N of force can, in effect, represent the measured gripping power to the silicone balloon (simulating tissue) of the IE bands, including additional gripping power of the tissue-gripping features such as the delta-shaped structures and recesses discussed above. Because the cross linked grip force of the IE bands was approximately 33% higher, this equates to 33% less slipping of the band when placed on tissue and/or 33% increased anti-slip ability of the IE bands. This can be caused at least in part by the tissue-gripping features formed on the tissue-contacting surfaces. Thus, these results can demonstrate the effectiveness of the tissue-gripping features (such as the delta-shaped structures) in providing significantly more ability to grip tissue by the IE bands compared to smooth bands such as the BSC bands. Because band slippage is a significant complication in band ligation medical procedures, the increased ability to grip tissue and prevent or reduce slippage of the bands translates into an important clinical advantage. The bands can thus greatly reduce surgical complications and provide better outcomes for patients and surgeons.

Example 3: Variceal Tissue

Figure 7:
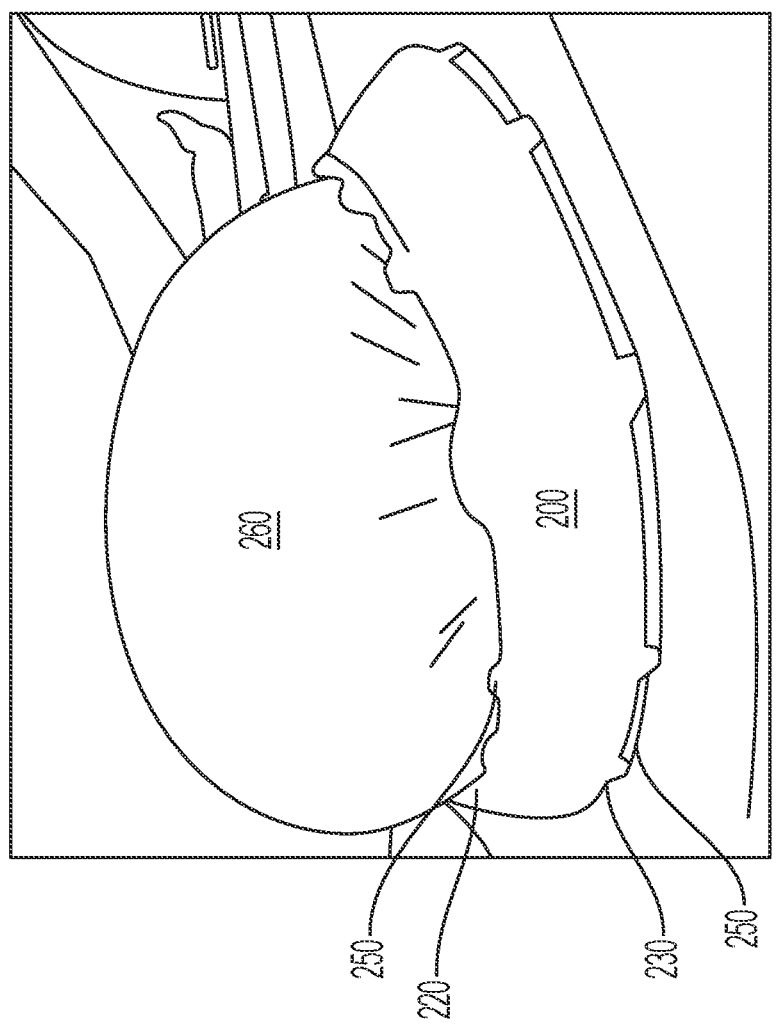
FIG. 7 is a perspective view of another embodiment of a ligation band applied to tissue.

FIG. 7 illustrates an embodiment of a ligation band 200, similar to the band 100 discussed above, with first and second tissue-contacting surfaces 220, 230 and tissue-gripping features 250, similar to the surfaces 120, 130 and the features 150. The figure illustrates the pressure being applied by the band 200 and the first and second surfaces 220, 230 to sandwich or secure trapped variceal tissue 260 therebetween, while the tissue-gripping features 250 provide extra anti-slip friction to lock or secure the variceal tissue 260 into place.

Example 4: Syndaver Synthetic Tissue

Figure 8:
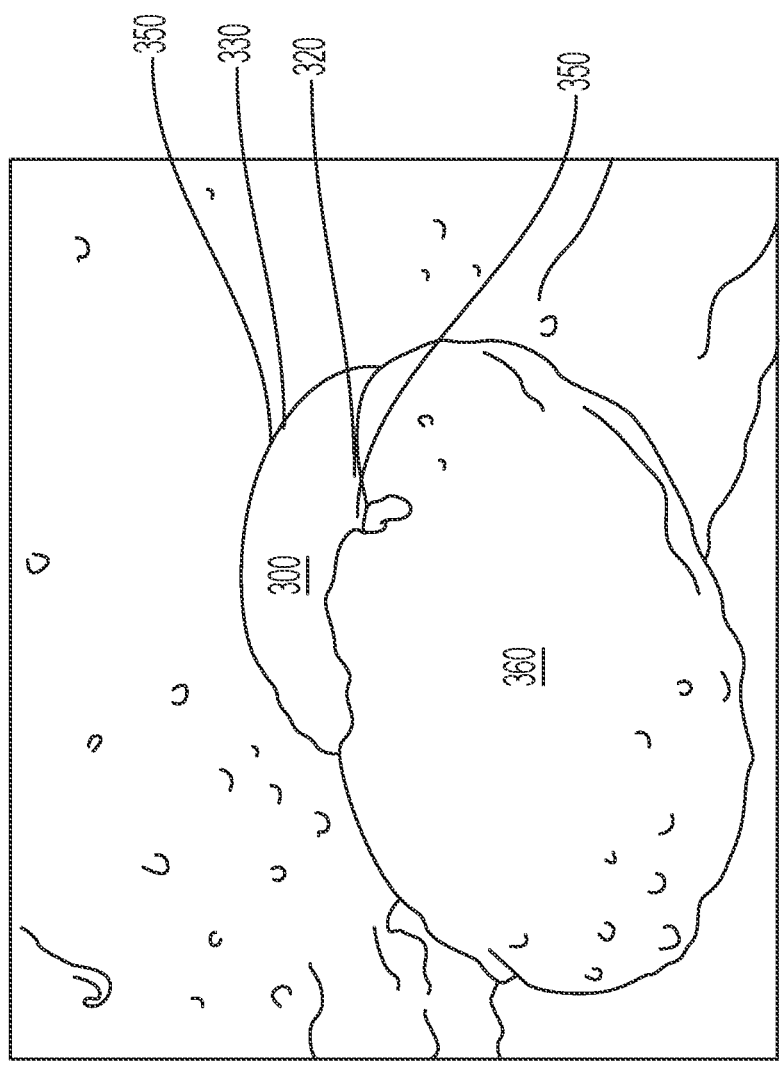
FIG. 8 is a perspective view of another embodiment of a ligation band applied to tissue.

FIG. 8 illustrates an embodiment of a ligation band 300, similar to the band 100, with first and second tissue-contacting surfaces 320, 330 and tissue-gripping features 350, similar to the surfaces 120, 130 and the features 150. The figure illustrates Syndaver synthetic tissue 260 being trapped by the tissue-gripping features 350. The pressure of the ball of the tissue 360 to pass through the aperture in the band 300 is met by the friction of the tissue-gripping features 350. Combined with enhanced radial force produced in part by the shapes of the tissue-gripping features 350, the result is better band retention and less chance of an immediate or delayed band slippage event.

Example 5: Delivery View of a Surgeon

Figure 9:
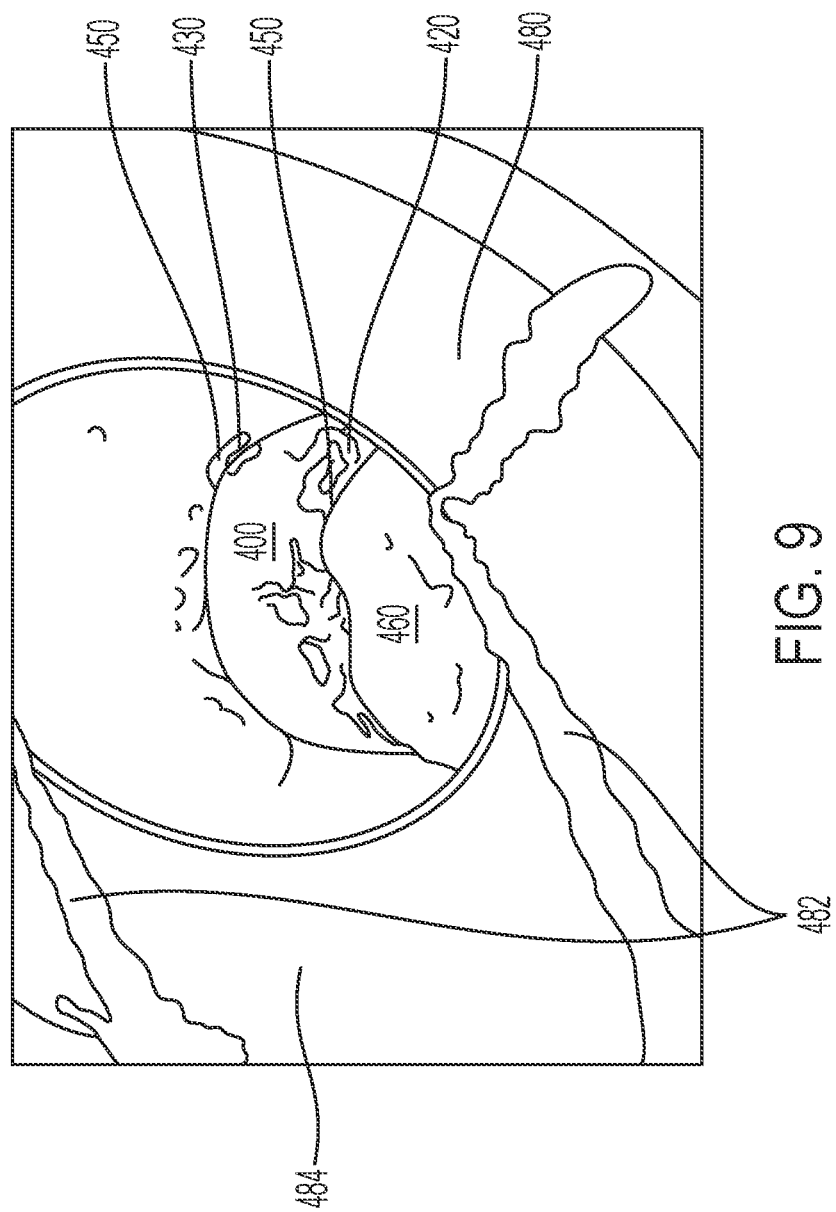
FIG. 9 is a perspective view taken along a barrel of an exemplary delivery device showing another embodiment of a ligation band applied to tissue.

FIG. 9 illustrates an embodiment of a ligation band 400, similar to the band 100, with first and second tissue-contacting surfaces 420, 430 and tissue-gripping features 450, similar to the surfaces 120, 130 and the features 150. The figure illustrates a view of a surgeon during delivery of the band 400. Delivery cords 482 of a delivery device 480 are seen through a delivery barrel 484. The band 400 has been placed on a varix 460, and the varix is starting to turn a dark brown or purple due to restriction of blood flow, which will eventually lead to necrosis and tissue death. Friction can be created by the first surface 420 of the band 400 on the tissue to retain against slippage, and the second surface 430 also provides friction on a mucosal base of the tissue to lock or secure the band 400 into place.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

What is claimed is:

1. A ligation band, comprising:
   a substantially ring-shaped elastic body having a first tissue-contacting surface, a second tissue-contacting surface opposite the first tissue-contacting surface, and an aperture extending therethrough, wherein at least one of the tissue-contacting surfaces has a plurality of protrusions formed thereon that define an interlinking web-pattern with a plurality of recesses therebetween;
   wherein the aperture is configured to receive and engage tissue of a patient to attach the ring-shaped elastic body to the tissue;
   wherein the protrusions of the at least one of the tissue contacting surfaces are configured to engage adjacent tissue to the tissue engaged by the aperture such that a portion of the adjacent tissue extends into the recesses to maintain the ring-shaped elastic body in a desired position relative to the tissue engaged by the aperture.

2. The ligation band of claim 1, wherein the elastic body is latex-free.

3. The ligation band of claim 1, wherein the plurality of protrusions are in a repeating delta pattern.

4. The ligation band of claim 1, wherein the plurality of protrusions are on both the first and second tissue-contacting surfaces.

5. The ligation band of claim 1, wherein the aperture is substantially cylindrical with smooth inner-facing sidewalls.

6. The ligation band of claim 1, wherein the ligation band has a compression force of at least about 5.5 N when expanded to 7.5 mm.

7. The ligation band of claim 1, wherein the ligation band has a compression force of at least about 6.5 N when expanded to 9 mm.

8. The ligation band of claim 1, wherein an average cross linked band grip force of the ligation band is at least about 0.50 N.

9. A ligation band, comprising:
a substantially ring-shaped elastic body having first and second tissue-contacting surfaces thereon and a central opening extending therethrough, each of the first and second tissue-contacting surfaces having four delta-shaped protrusions projecting therefrom and spaced around the central opening, each delta-shaped protrusion defining a substantially delta-shaped recess therein and each delta-shaped protrusion being configured to grip tissue;
wherein the central opening is configured to receive and engage tissue of a patient to attach the ring-shaped elastic body to the tissue:
wherein the delta-shaped protrusions are configured to engage adjacent tissue to the tissue engaged by the central opening such that a portion of the adjacent tissue extends into the delta-shaped recesses to maintain the ring-shaped elastic body in a desired position relative to the tissue engaged by the central opening.

10. The ligation band of claim 9, wherein the four delta-shaped protrusions define an interlinking web-pattern.

11. The ligation band of claim 9, further comprising 3 perimeter recesses formed between each adjacent delta-shaped protrusion on the first and second tissue-contacting surfaces.

12. The ligation band of claim 9, wherein each delta-shaped protrusion has an apex oriented away from the central opening.

13. The ligation band of claim 9, wherein the ligation hand has a compression force of at least about 5.5 N when expanded to 7.5 mm.

14. The ligation band of claim 9, wherein the ligation band has a compression force of at least about 6.5 N when expanded to 9 mm.

15. The ligation band of claim 9, wherein the elastic body is synthetic polyisoprene.

\* \* \* \* \*